(12) United States Patent  
Vellinger et al.

(10) Patent No.: US 7,198,940 B2  
(45) Date of Patent: Apr. 3, 2007

(54) BIOREACTOR APPARATUS AND CELL CULTURING SYSTEM

(75) Inventors: John C. Vellinger, Floyd Knobs, IN (US); Kenneth W. Barton, Greenville, IN (US); Mark S. Deuser, Floyd Knobs, IN (US); Mark E. Wells, Athens, AL (US)

(73) Assignee: Shot Hardware Optimization Technology, Inc., Greenville, IN (US)

( * ) Notice: Subject to any disclaimer, the term of this patent is extended or adjusted under 35 U.S.C. 154(b) by 0 days.

(21) Appl. No.: 10/003,481

(22) Filed: Oct. 25, 2001

(65) Prior Publication Data

US 2002/0146816 A1 Oct. 10, 2002

Related U.S. Application Data

(60) Provisional application No. 60/243,121, filed on Oct. 25, 2000.

(51) Int. Cl.  
*C12M 1/36* (2006.01)

(52) U.S. Cl. .............................. 435/286.5; 435/288.7; 435/303.1; 435/303.3; 435/309.2; 435/809; 435/297.2; 435/298.2

(58) Field of Classification Search ............. 435/284.1, 435/286.5, 289.1, 297.2, 297.4, 303.1, 303.3, 435/809; 422/99, 104  
See application file for complete search history.

(56) References Cited

U.S. PATENT DOCUMENTS

| | | |
|---|---|---|
| 3,264,739 A | 8/1966 | Berlinsky et al. |
| 3,540,700 A | 11/1970 | Freedman |
| 3,676,074 A | 7/1972 | Shibayama et al. |

(Continued)

FOREIGN PATENT DOCUMENTS

GB 1562686 A * 3/1980

(Continued)

*Primary Examiner*—William H. Beisner  
(74) *Attorney, Agent, or Firm*—Carrithers Law Office PLLC; David W. Carrithers

(57) ABSTRACT

A bioreactor apparatus and cell culturing system is provided for the automated cultivation and processing of living cells remotely both on earth and in low gravity which utilizes a generally cylindrical reactor vessel that may be optionally rotated about its cylindrical axis while allowing the entrance of fresh or recycled fluid and the removal, optionally, of spent medium, medium to be recycled or filtered or unfiltered medium for the collection of samples. A method of exchanging gases between the culture medium and ambient gases is provided. A fresh-medium storage bag and peristaltic pump is used for batch feeding, perfusion or sample collection. An enclosure and manifold representing an additional level of chemical containment and a series of pinch valves for the periodic collection of samples of suspended cells or cell-free medium is disposed therein together with a humidity control system. The bioreactor is computer controlled in order to control all functions including rotation of the reactor vessel, feeding fresh medium, perfusing the reactor vessel, timed collection of samples of fluid from the reactor, selecting between collecting cells or cell-free supernatant. A sealed compartment for sample-collection bags provides a level of chemical containment for safety. A sealed external housing is used for all components of the device except the power supply and computer. An external loop and electronic video microscope provides real-time and recorded and/or transmitted observation of cells in the suspension.

26 Claims, 15 Drawing Sheets

U.S. PATENT DOCUMENTS

| | | |
|---|---|---|
| 3,769,176 A | 10/1973 | Hise et al. |
| 3,812,016 A | 5/1974 | Müller |
| 3,911,619 A | 10/1975 | Dedolph |
| 3,925,165 A | 12/1975 | Müller |
| 4,161,172 A * | 7/1979 | Pickering ................ 600/22 |
| 4,208,483 A | 6/1980 | Lee |
| 4,310,630 A | 1/1982 | Girard et al. |
| 4,343,904 A | 8/1982 | Birch et al. |
| 4,373,029 A | 2/1983 | Nees |
| 4,377,639 A | 3/1983 | Lee |
| 4,537,860 A | 8/1985 | Tolbert et al. |
| 4,605,626 A | 8/1986 | Beck |
| 4,618,586 A * | 10/1986 | Walker ................ 435/286.5 |
| 4,649,117 A | 3/1987 | Familletti |
| 4,650,766 A * | 3/1987 | Harm et al. ........... 435/286.6 |
| 4,720,462 A | 1/1988 | Rosenson |
| 4,749,654 A | 6/1988 | Karrer et al. |
| 4,988,623 A | 1/1991 | Schwarz |
| 5,026,650 A | 6/1991 | Schwarz et al. |
| 5,153,131 A | 10/1992 | Wolf et al. |
| 5,153,133 A | 10/1992 | Schwarz et al. |
| 5,155,034 A | 10/1992 | Wolf et al. |
| 5,155,035 A | 10/1992 | Schwarz et al. |
| 5,376,548 A * | 12/1994 | Matsuo et al. ........... 435/297.2 |
| 5,424,209 A * | 6/1995 | Kearney ............... 435/286.5 |
| 5,437,998 A * | 8/1995 | Schwarz et al. ........ 435/298.2 |
| 5,665,594 A | 9/1997 | Schwarz |
| 5,702,941 A | 12/1997 | Schwarz |
| 5,763,279 A | 6/1998 | Schwarz et al. |
| 5,882,918 A * | 3/1999 | Goffe .................. 435/286.6 |
| 6,008,010 A * | 12/1999 | Greenberger et al. ........ 435/41 |
| 2002/0110905 A1 * | 8/2002 | Barbera-Guillem et al. ..... 435/294.1 |

FOREIGN PATENT DOCUMENTS

| | | | |
|---|---|---|---|
| JP | | 03160980 A * | 7/1991 |
| WO | | WO 9002171 A1 * | 3/1990 |

* cited by examiner

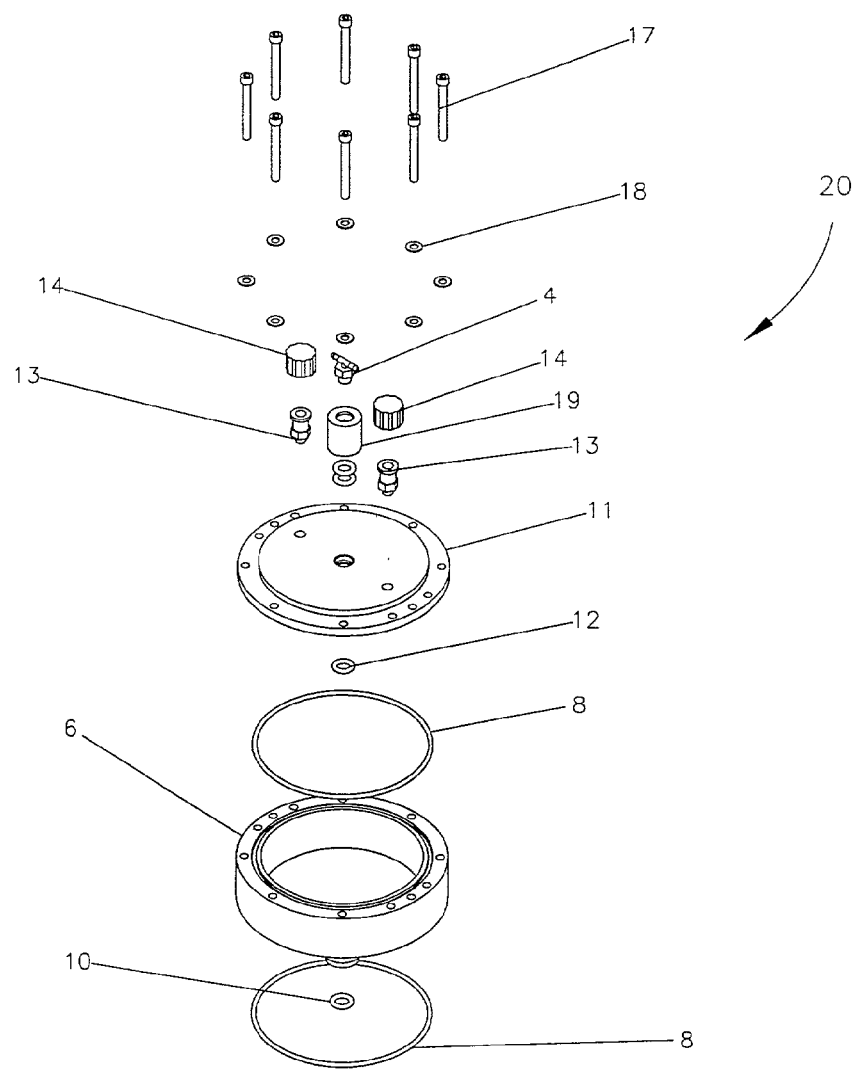
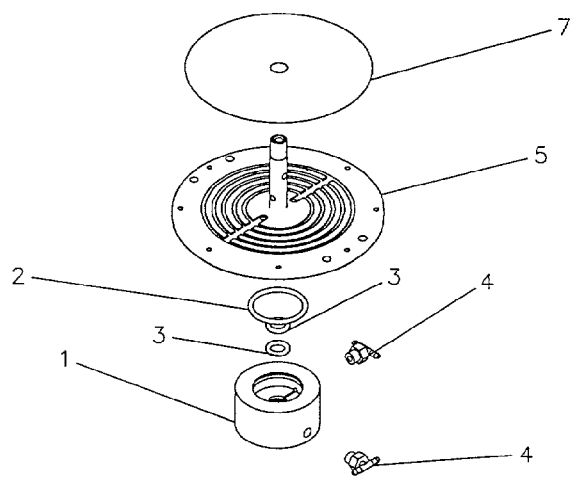
Figure 1

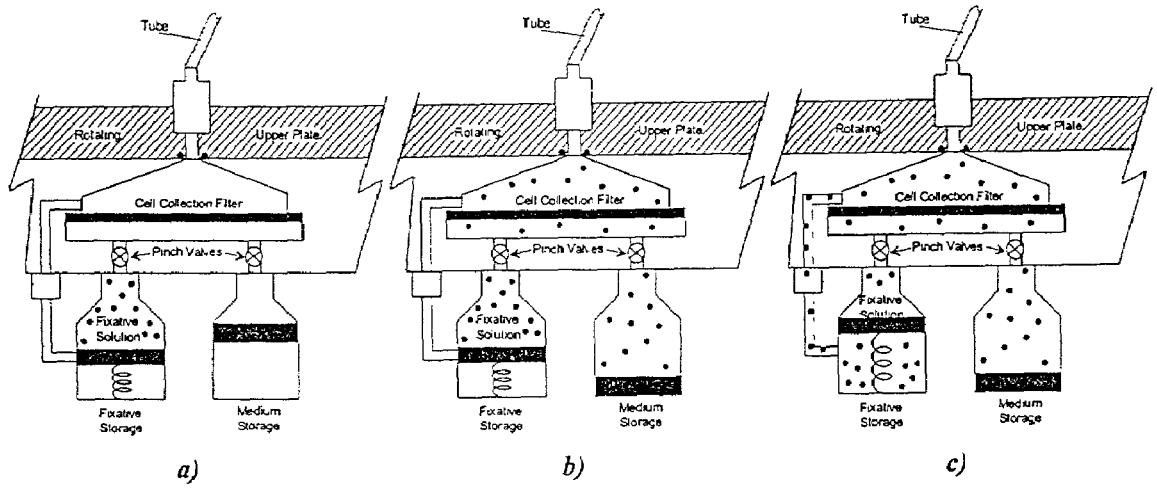

a) This position represents the collection syringes before a sample is collected.
b) The pinch valve for the medium is opened. The cells remain on the filter material while the medium pushes the syringe plunger down. The pinch valve is closed.
c) The pinch valve for the fixative syringe is opened. The fixative lifts the cells off of the filter material and the pressure forces the liquid to the backside of the syringe. The pinch valve is closed.

Figure 7

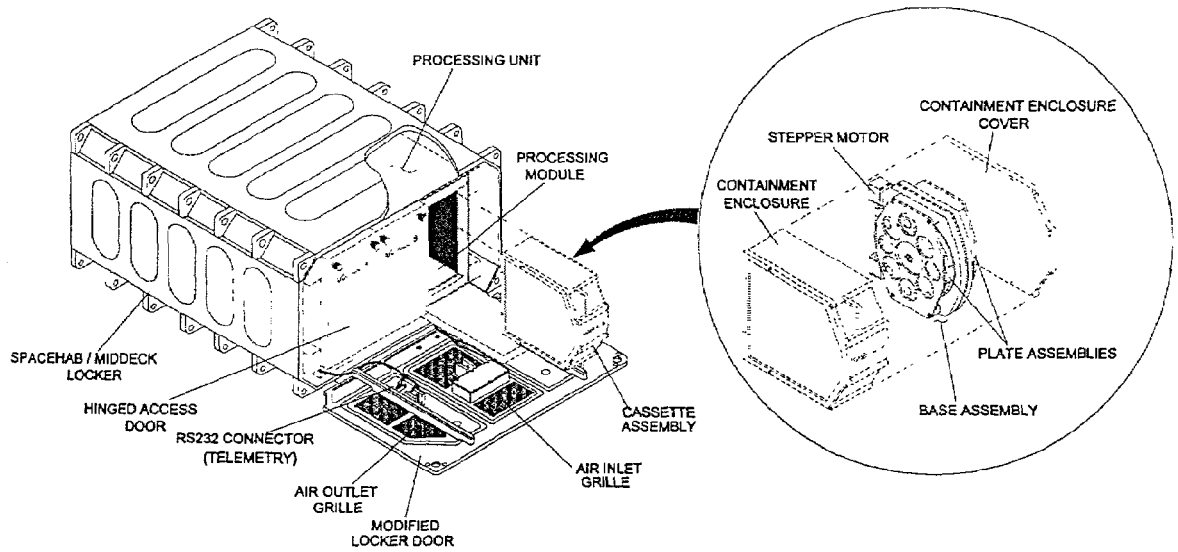
Figure 16                                        Figure 15

BIOREACTOR APPARATUS AND CELL CULTURING SYSTEM

This application claims priority from U.S. Provisional Application Ser. No. 60/243,121 filed on Oct. 25, 2000. This application is part of a government project, Contract No. NAS8-98120.

FIELD OF THE INVENTION

The invention relates to the field of a fully-automated perfused cell-culture bioreactor system (laboratory in a cassette).

DESCRIPTION OF THE PRIOR ART

There are a number of investigations being conducted on cell growth in specialty bioreactors, which could potentially benefit from use of our device. The research has application in areas as diverse as tissue engineering and transplantation, cancer research and even insect culture and the potential of generating products from cells grown in microgravity. General areas include implantable cartilage tissue grown on artificial scaffolds; cardiac muscle tissue to study drug effects on muscle disease; HIV pathogenesis studies in lymphoid cells; evaluation of renal toxicity; and colon, ovarian, breast, and prostate cancer models A new discipline in the area of cell culture is emerging. Tissue Engineering is basically the growth of any tissue or organ by applying principles of chemical and physical modifications to the environment, including use of special bioreactors to create three-dimensional cultures. A number of biotechnology companies are currently working on processes in which external forces may be used to control cells and their products and to possibly confer differentiation ability. Tissue modeling, architecture and differentiation depends on the arrangement and juxtapositioning of interacting cells. The gentle environment provided for cell culture in the bioreactor described and claimed herein should optimize conditions for tissue formation. In conventional bioreactors with stirring devices, the degree to which cell aggregates increase in size depends on the rate of formation and the rate of destruction of the cellular bridges. Principles of tissue engineering in microgravity using the present invention are applicable to regrowth of nerve tissue. Mammalian neuronal precursor cells in vitro can make graft therapy a practical approach to the treatment of such neurological diseases as Parkinson's, Alzheimer's and Huntington's disease. The limited availability of transplant tissue seriously limits this type of treatment.

In the area of diabetes research, proislet cells prepared from human fetal pancreatic proislets and maintained in vitro in the presence of endocrine growth factors (IGF-1) may provide a source of tissue with enriched beta-cell activity and may be suitable as a source of transplantable tissue. For successful transplantation of pancreatic cells, it is necessary to remove the immunogenic cells present in the preparation. Culture of pancreatic preparations in the rotating bioreactors can be a model for determining the presence of immunogenic cells in the cultured pancreatic isolates. In other areas of research utilizing bioreactors, European researchers have characterized cultured yeast cells grown in microgravity in bioreactors and monoclonal antibody production in bioreactor systems as an alternative to production in mice suggests feasibility of using bioreactors instead of mice for antibody production.

Cell survival in culture is dependent on the transfer of nutrients and oxygen to the cells and removal of spent metabolites from the local vicinity of cells. For the low-shear mixing, it is necessary to impart a low level of fluid motion to create effective mixing of the fluid in the cell reactor. One of the most important attributes of the rotating-wall reactor technology is the ability to grow cells in a low-shear environment to attain higher cell densities than in conventional stirred bioreactors. The trade-off is that cell density must be balanced with the ability of the system to supply nutrients and remove spent metabolites while maintaining pH and $CO_2$ levels within acceptable ranges.

SUMMARY OF THE INVENTION

A bioreactor apparatus and cell culturing system is provided for the automated cultivation and processing of living cells remotely both on earth and in low gravity which utilizes a generally cylindrical reactor vessel that may be optionally rotated about its cylindrical axis while allowing the entrance of fresh or recycled fluid and the removal, optionally, of spent medium, medium to be recycled or filtered or unfiltered medium for the collection of samples. The bioreactor vessel a cylindrical wall, two cover plates, two rotary unions, fill ports, and a polymeric filter. A method of exchanging gases between the culture medium and ambient gases is fabricated from a user-selected length of permeable tubing and a peristaltic pump. A polymeric fresh-medium storage bag and peristaltic pump is used for batch feeding, perfusion or sample collection. A sealed compartment for sample-collection bags provides a level of chemical containment for safety. More particularly, an enclosure and manifold representing an additional level of chemical containment and a series of pinch valves for the periodic collection of samples of suspended cells or cell-free medium is disposed therein together with a humidity control system consisting of a polymeric porous matrix and a fan. A computer program with graphical user interface for automatically and/or robotically controlling all functions especially including rotation of the reactor vessel, feeding fresh medium, perfusing the reactor vessel, timed collection samples of fluid from the reactor, selecting between collecting cells or cell-free supernatant. A sealed external housing is used for all components of the device except the power supply and computer. All polymeric components are made of low-flammability, non-toxic, heat-resistant polymers such as polycarbonate, polysulfone, polypropylene, polytetrafluoroethylene, or silicone.

The bioreactor apparatus and cell culturing system preferably includes a rotary multiple sample collector with capability for collecting cells on filters, fixing the cells and collecting the cells.

The rotary sample collector includes a rotating inlet into a compartment with a filter, means to remove waste liquid from an input cell suspension, means for collecting cells in chambers in liquid suspension, and means to store fixed cells for later recovery and examination.

The bioreactor and cell culturing system of the present invention provides many advantages over conventional bioreactors. The features include, but are not limited to, options for gentle mixing of cell and/or microcarrier suspensions (rotation of vessel and/or impeller), independently variable perfusion and oxygenation rates, pH and oxygen monitoring, real-time imaging of cells in an external loop, compact design, computerized and automated control of all functions, user-friendly access and operation, and flexible options for automated collection of samples of cells and/or cell-free media during each experiment. The instant bioreactor will fit conveniently into a cassette with a volume less than 2.0 L (space-flight version) or on a single shelf of a standard tissue culture incubator.

The bioreactor of the present invention includes dual channel lower fluid unions, a low-pressure-drop filter which utilizes novel methods to prevent cell capture on the filter. A video camera system integrates a miniature camera, stopped-flow microscopic observation slide, and LED backlighting optics. The device incorporates analytical sensors to measure pH and oxygen. The novel rotary cell sample collector utilizes an upper and lower collector plate, a drive mechanism to rotate the upper plate, and utilizes sample collection syringes. The system further includes the cell growth reactor, rotary cell sample collector, CCD camera, sensors, and the peristaltic pump. Table 1 sets forth the general parameters of a preferred embodiment as follows:

TABLE 1

Hardware Requirements and Specifications, Subsystems

Cell Growth Reactor

Sample Volume- 50 ml
Rate of Rotation- 6 RPM (uniform rotation)
Upper Rotary Union- 1 inlet
Lower Rotary Union- 2 independent outlets for:
   1. Medium Only (Cells are filtered)
   2. Medium and Cells
Capability To Add Medium Upon Demand
Transport Viewing Surface for Video Observations
Oxygenation of the Medium in the Reactor
Sample Port for Loading and Unloading
Reactor Materials Compatible with Cell Growth Miniature Peristaltic Pump Deliver Medium Solution to Cell Growth Reactor
Circulate Medium Into/Out-of Cell Growth Reactor CCD Camera System Video Frame Grabber: 1 frame per 30 seconds
Beam Splitter for Dual Optical Viewing of:
   1. Cell Growth Reactor
   2. Microscopic Observation Slide
Optimal LED Backlights Sensor System Continuous measurement of pH
   1. Ability to autoclave/disinfect electrodes
   2. Monitor pH level range of 6.5 to 7.5
Glucose Monitoring Rotary Cell Sample Collector Collect Fixed Cell: 6–8 samples
Collect Medium: 6–8 samples The bioreactor cassette fluid unions provide the capacity to add growth medium, to extract spent medium, to collect cell samples.

The instant bioreactor also provides three fluid flow paths, the feed cell flow path, sample collection flow path, and aeration flow path. The fluid flow path delivers medium from the storage bag to the bioreactor when the cells need nourishment or when a medium sample is collected. The sample collection flow path delivers medium from the bioreactor to sample collection bags or cuvettes. The aeration flow path circulates the medium through the silicone tubing in an ambient or oxygen enriched environment whereby oxygen passes through the tubing oxygenating the medium.

The present invention utilizes pinch valves between the sample containers, waste container, and a sample manifold in order to isolate samples.

An advantage of the present invention as compared to conventional bioreactors is that the system allows samples of both filtered (no cells) and unfiltered (with cells or particles) media to be extracted automatically during bioreactor operation. Cell filtration takes place internal to the reactor. Both cell and media sample extraction take place thorough the concentric nested exists into the lower rotary fluid union.

The instant bioreactor provides a large filtration area with respect to the small bioreactor size. This feature minimizes both the pressure drop across the filter, (and in turn the system working pressure), and the fluid velocity through the filter (minizing cell attachment and clogging of the filter).

The instant bioreactor hub design is unique in that the central rotation hub encompasses more than one fluid outlet. The hub also contains the filter support surface. The design is simple and has a miminal parts count. The hub provides alignment for the bioreactor component stack which includes the lower fluid union, hub, filter, spacer, upper cover, and upper fluid union.

Moreover, the present invention incorporates the bioreactor into a system utilizing a rotation drive and perfusion pump, sampling system, and pressure relief system. The system provides a means for cell sampling, dilution, and fixation.

The valve design allows the distribution valve to utilize pinch valve features without using multiple pinch valves to minimize the use of serialized tubing (serialized tubing versus having to sterilize the valve as is often required with conventional systems).

It is an object of the present invention to include the following features: a cell chamber volume, perfused system, zero head space, variable temperature control, teleoperation as an option, 1G centrifuge adaptable, oxygenation capability, capable of utilizing microcarriers, capable of maintaining long term cultures, multiple individual sample containers, interval sampling capability, fixation at selected times, filtration of cells from medium, automated delivery of fixative, sample storage of between 4 and 20 degrees centigrade, physiological sensors for pH, glucose, oxygen, etc., addition of activators to culture chambers, and the ability to be automated and self contained.

It is an object of the present invention to provide a flow-through bioreactor whereby the interior surfaces of the bioreactor's fluid volume are smooth to minimize the likelihood of cell attachment.

It is an object of the present invention to provide a temperature control system capable of controlling the temperature from −4° C. to 38° C. and preferably at about 37° C.

It is an object of the present invention to provide a sample collection capability of one or more independent samples.

It is an object of the present invention to provide a means of collecting different types of cells or to collect only cells or particles, only media, or both.

It is an object of the present invention to provide a capability to separate cells from culture medium for sampling.

It is an object of the present invention to provide a medium which is replenishable by means of perfusion which is programmable or active on demand.

It is an object of the present invention to provide a medium for continuous oxygenation.

It is an object of the present invention to provide a means of gently mixing of cell and or particles in the medium by rotation or impeller.

It is an object of the present invention to provide as an option a circulation fan to maintain uniform gas exchange and thermal control.

It is an object of the present invention to provide a means for humidity control.

It is an object of the present invention to provide a means of providing the apparatus in a modular cassette in order to facilitate sequential and/or parallel experiments.

It is an object of the present invention to provide a means for the researcher to have experiment flexibility and select solutions, temperatures, and sampling times.

It is an object of the present invention to provide a means for collecting samples of cells, particles, or medium in bags, cuvettes, syringes, or other vessels.

It is an object of the invention to provide means for disassembling the cell growth reactor for autoclaving.

It is an object of the present invention to provide a bioreactor cell culturing system designed to be utilized in a cassette integrated within a space flight processing facility.

These and other objects of the present invention will be more fully understood from the following description of the invention.

BRIEF DESCRIPTION OF THE DRAWINGS

A better understanding of the present invention will be had upon reference to the following description in conjunction with the accompanying drawings in which like numerals refer to like parts throughout the several views and wherein:

FIG. 1 is an exploded view showing the components of a preferred embodiment of the bioreactor vessel;

FIG. 7 is a flow diagram of the present invention showing the sequence for the rotary cell sample collector;

FIG. 15 is a perspective cutaway view showing a cassette within a containment enclosure comprising a cassette assembly for insertion into a middeck locker processing facility; and FIG. 16 is a perspective cutaway view showing a middeck locker processing facility.

DESCRIPTION OF THE PREFERRED EMBODIMENT

Figure 2:
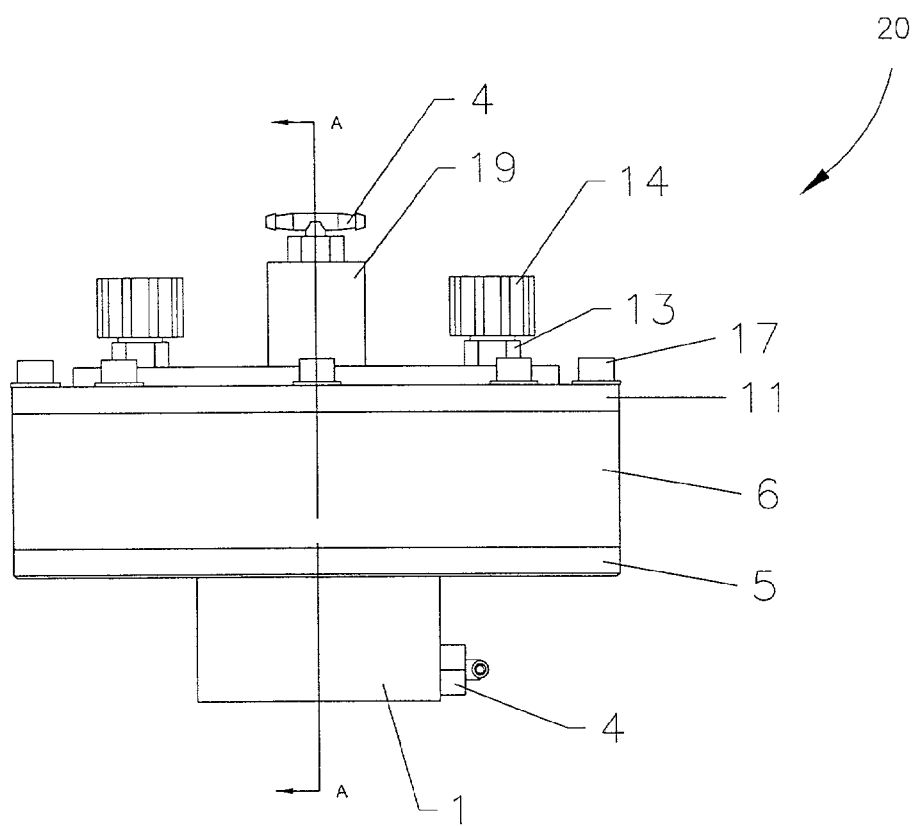
FIG. 2 is an elevational side view of the present invention showing the assembled bioreactor vessel of FIG. 1.

A device for the Automated Cultivation and Processing of Living Cells Remotely and in Low Gravity is generally designated 100 in the drawings. As set forth in the drawings, the individual components of the device 100 will first be identified and the operation of, and fluid flow through, device 100 will then be described.

Figure 3:
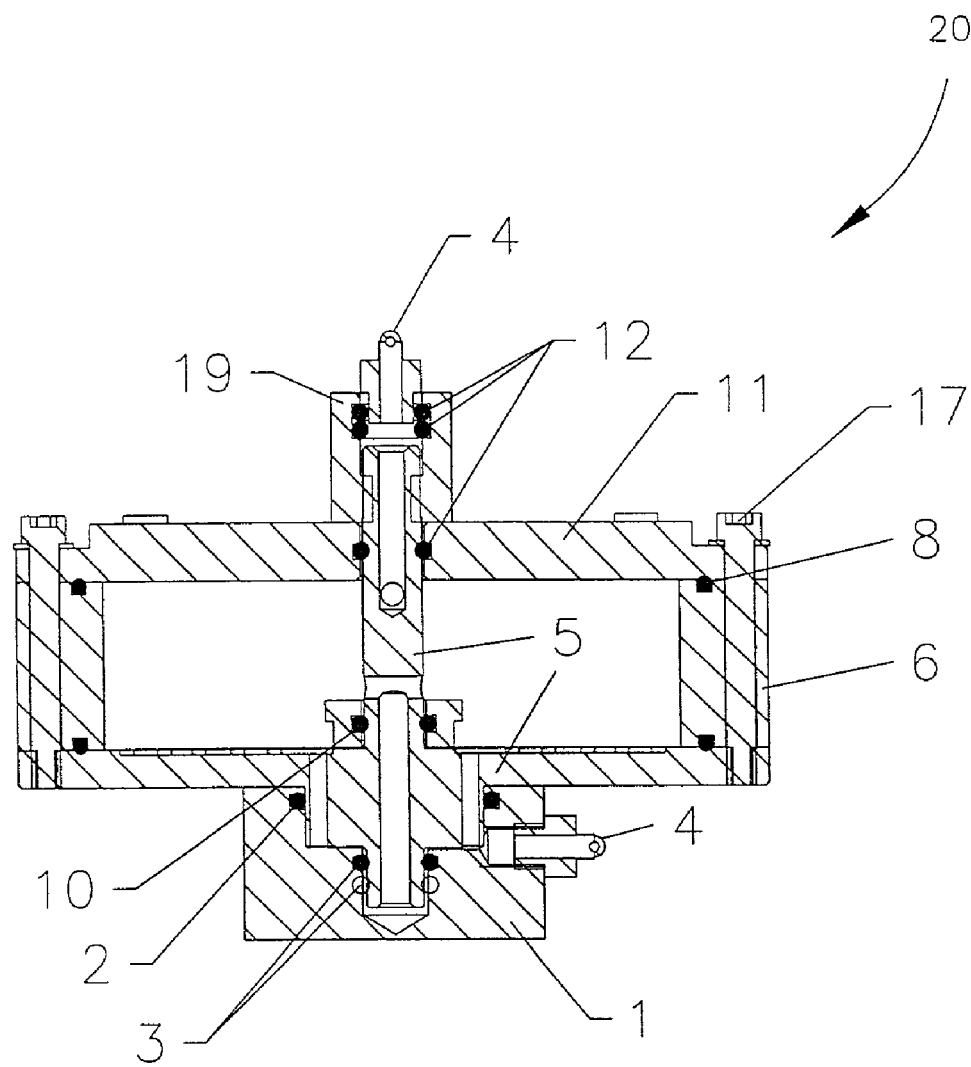
FIG. 3 is a cross sectional view of the present invention along lines 3—3 of the reactor vessel of FIG. 1 showing the seals and components assembly.

The cultivation and processing device includes a reactor vessel 20, which, as shown in detail in FIG. 1 consists of cylindrical wall 6 affixed to an upper cover 11 and lower cover 5 to which it is sealed by stationary O-rings 8. The upper cover plate is perforated by two fill ports 13 with relief-valve covers 14 and by a bearing hole for the tubular axle that is one piece with lower plate 5, which axle is capped at the top plate by upstream rotary union 19 and by bispout 4. The lower cover plate 5 supports a polymeric filter 7, which prevents cells from exiting the reactor when fluid is withdrawn through the upper one bispout of two bispouts 4 attached to downstream rotary union 1, which is sealed to the lower cover plate by O-rings 2 and 3. Cell-containing fluid is withdrawn through the lower one bispout of two bispouts 4 under the control of valves and pumps to be described in FIG. 5. The cylindrical wall, top cover plate and lower plate are secured together by machine screws 17 to assemble the reactor vessel as shown in FIGS. 2 and 3.

Figure 4:
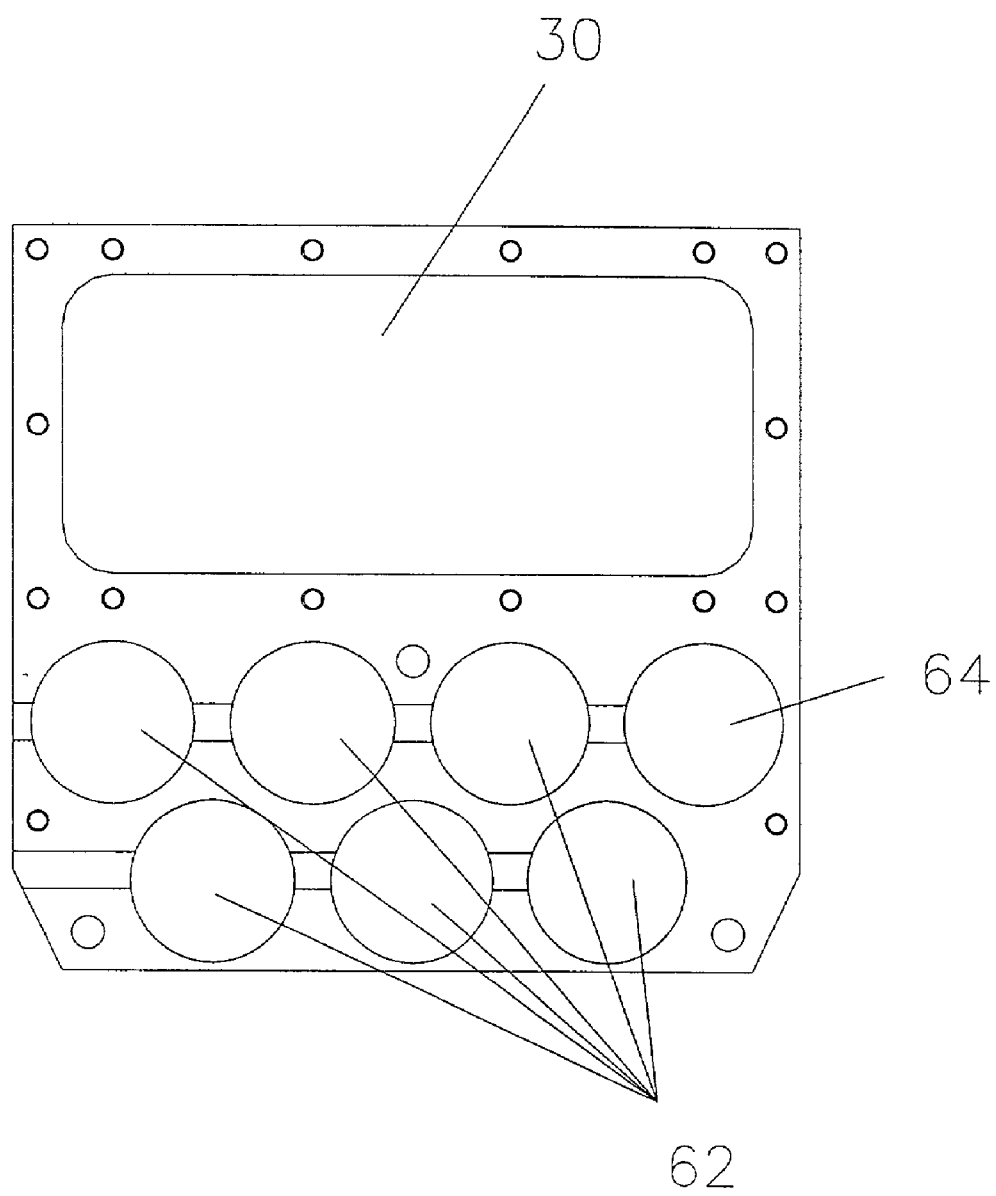
FIG. 4 is a plan view showing a sealed container of the present invention for sample collection bags and the positioning of pinch valves.

When samples are withdrawn for later study, fluid is pumped into one of more or less than six partially evacuated sample bags 35, which are housed in a sealed compartment 30 shown in FIG. 4. The bags 35 in sealed compartment 30 may contain formaldehyde fixing solution or RNA extracting solution or a solution of any reagent or any solid reagent with which the experimenter wishes the withdrawn sample to react. Therefore, sealed compartment 30 represents a third level of containment in the embodiment of the device 100 shown in FIG. 6 and allows the housing of solutions of Hazard Level 2 therein. Withdrawn samples enter the bags 35 in the sealed compartment 30 through tubing connectors 32 that perforate, manifold-style, one wall of sealed compartment 30.

Figure 5:
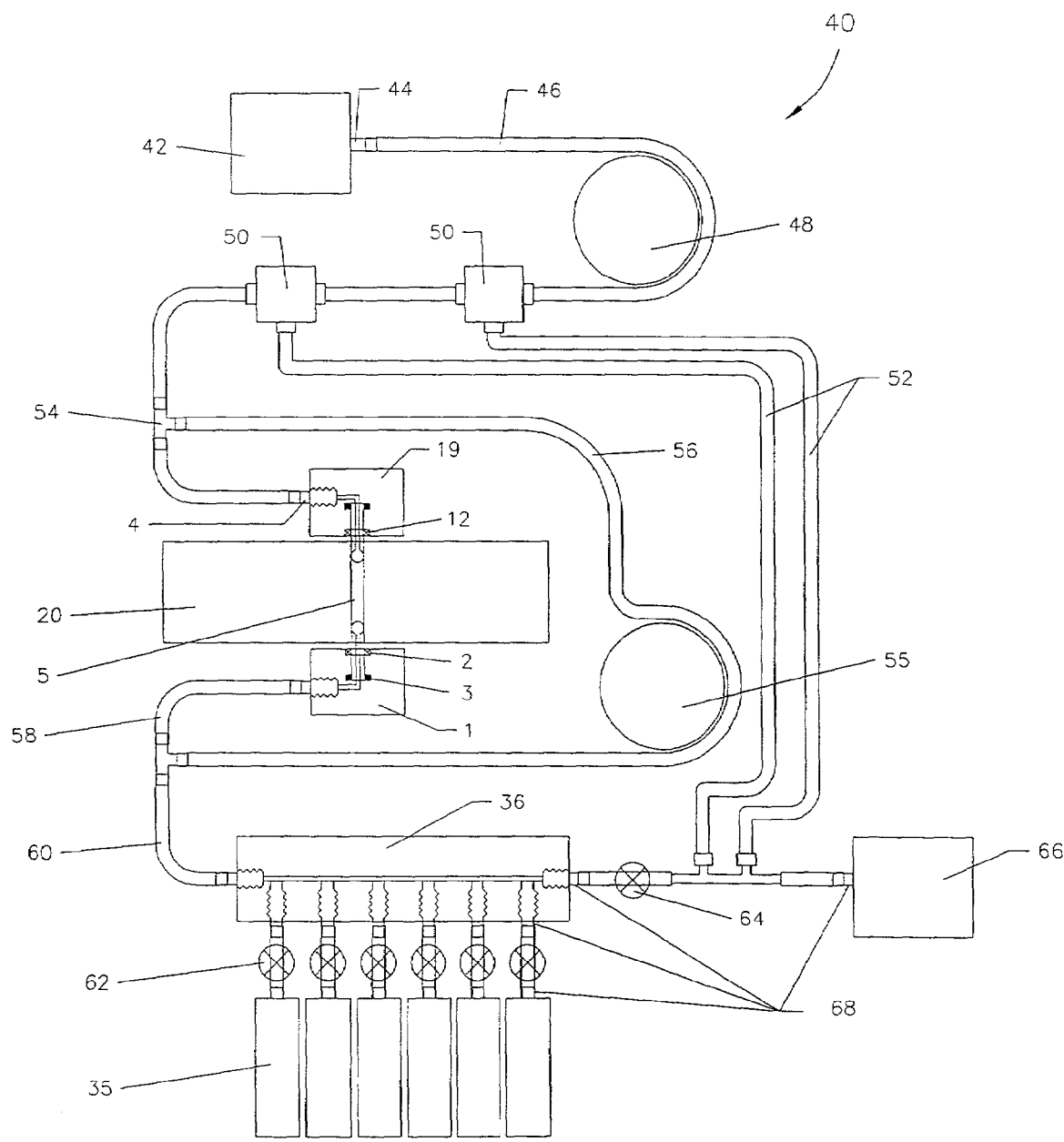
FIG. 5 is a schematic diagram of the present invention showing a fluid handling subsytem flow path.

The functioning of the device for the Automated Cultivation and Processing of Living Cells is best understood using the flow diagram in FIG. 5 of the drawings. A suspension of cells or cells attached to microcarrier particles or three-dimensional tissue or other planktonic organisms is maintained in a (usually, but not necessarily, nutrient) liquid medium in reactor vessel 20 as the primary goal of the Device. Feed liquid medium is stored in medium storage bag 42, which is connected to medium feed line 46 by barbed fitting 44. Medium is drawn through this line by peristaltic pump 48 and passed on to the reactor via T-fitting 54 and spout 4, which admits medium into the upstream rotary union 19 and the culture vessel 20. The bursting of the flexible tubing of feed line 46 and recirculation line 56 is prevented by pressure relief valves 50 that will shunt liquid directly to waste storage bag 66 in the event of an overpressure. At user's option peristaltic pump 55 may be used to pump medium through external loop 56, which may consist of gas-permeable tubing of various lengths up to approximately 1 m for exchange between gas dissolved in the medium and ambient gas or may serve a sensor (not shown) of the composition of the medium. The direction of flow through external loop 56 indicated by a curved arrow. To operate the reactor in continuous perfusion mode or in batch-fed mode peristaltic pump 48 supplies fresh fluid through rotary union 19 into the vessel, from which spent medium exits through rotary union 1 into exit lines 58 and 60, through open pinch valve 64 and into waste storage bag 66. For the collection of samples, one of the six solenoid pinch valves 62 is opened, peristaltic pump 55 is off, and peristaltic pump 48 operates to provide driving pressure and make-up volume for sample fluid.

The volume of the medium storage bag is 100 mL, that of the reactor vessel is 50 mL, and the volume of the waste storage bag is 100 mL in one possible embodiment. Typical volume of sample collection bags is 6 mL each, more or less.

Figure 6:
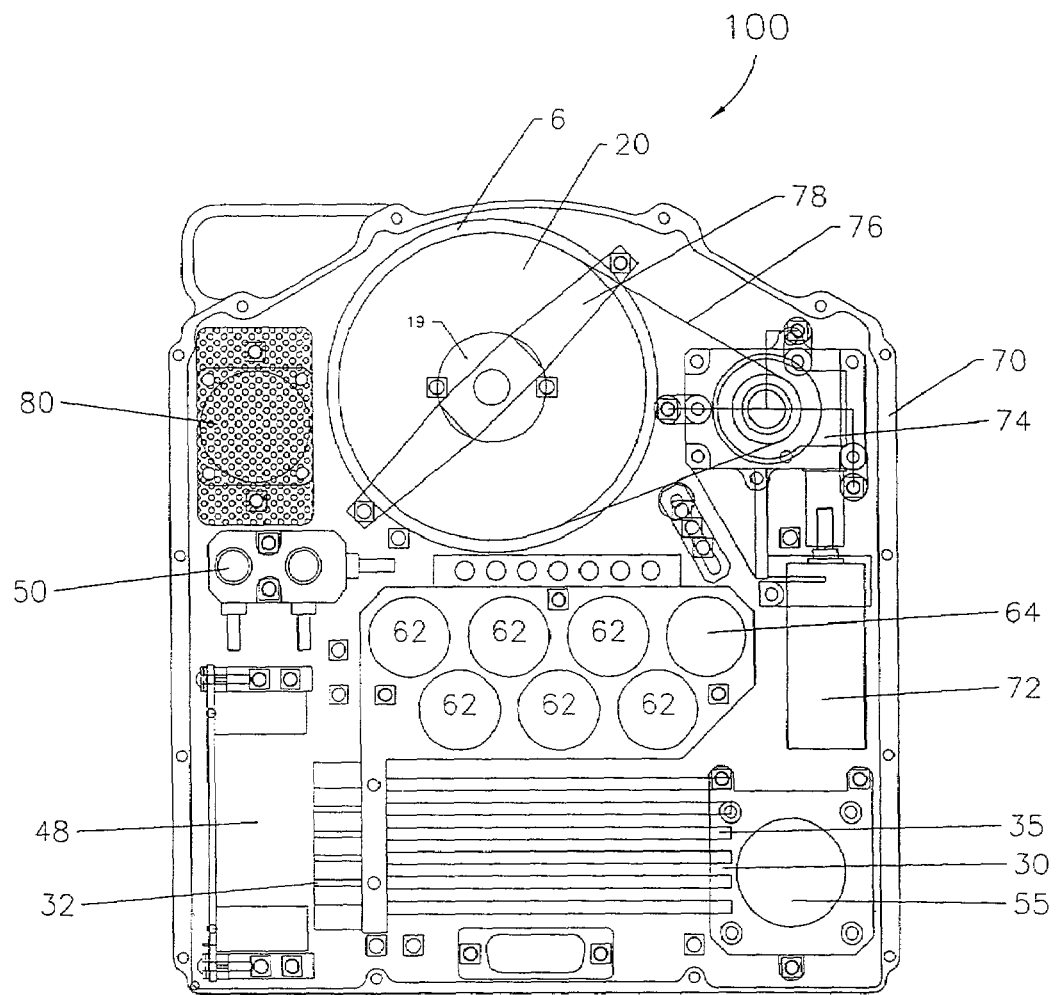
FIG. 6 is a plan view of the bioreactor of the present invention and automated cell cultivation and processing cassette unit.
Figure 8:
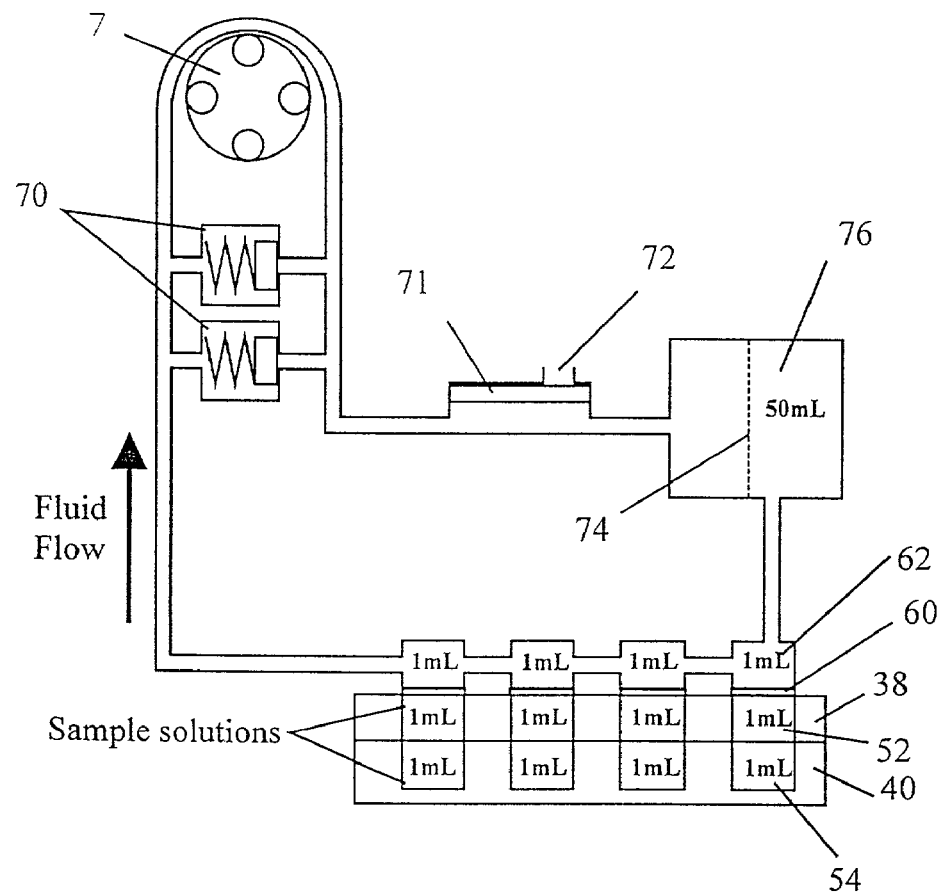
FIG. 8 is a flow diagram of the present invention showing the fluid flow path for the sample collection.

An embodiment of the Device, designed for cultivating cells automatically in space flight, is shown in FIG. 6 of the drawings. In addition to the components just described, a motor 72 is used, with a gearing mechanism 74 to drive belt 76, which causes reactor vessel 20 to rotate on its axis supported by yoke 78. Tubing is not shown. A water-saturated polymeric porous medium (sponge) 80 may be used to maintain humidity in the sealed housing 70, which provides one level of chemical containment for safety.

In all embodiments, a computer controls the functions of all energized parts, namely peristaltic pumps 48 and 55, solenoid pinch valves 62 and 64, humidification fan at 80 (not shown), and drive motor 72. A computer program with a Graphical User Interface (GUI) allows the user to sequence the events within the Device over periods of several days to weeks.

Application and Experimental Method

The 50 ml polycarbonate cell growth reactor as best shown in FIGS. 1—3, is the heart of the system, since it supports the growth and viability of the cells during an experiment. The interior surfaces of the cell growth reactor are smooth to eliminate any cell entrapment points while, in addition, the reactor is capable of rotating at rates up to 6 RPM to keep the cells in suspension. The rotation of the cell growth reactor is accomplished by using a timing belt wrapped around the reactor that is driven by a DC motor, which also drives the peristaltic pump head.

The cell growth reactor is optically transparent on the upper surface to permit video observations of the internal contents. The reactor also has several fill and extraction locations on the outside of the vessel. One side port and two top ports simplify the sample loading and unloading process for each experiment. The prototype units fabricated to date contain two fluid unions. One fluid union is located at the top of the reactor while the other fluid union is located at the bottom of the reactor. The rotary fluid unions allow the entry and removal of the medium solution with or without the cells while the reactor is rotating.

Figure 9:
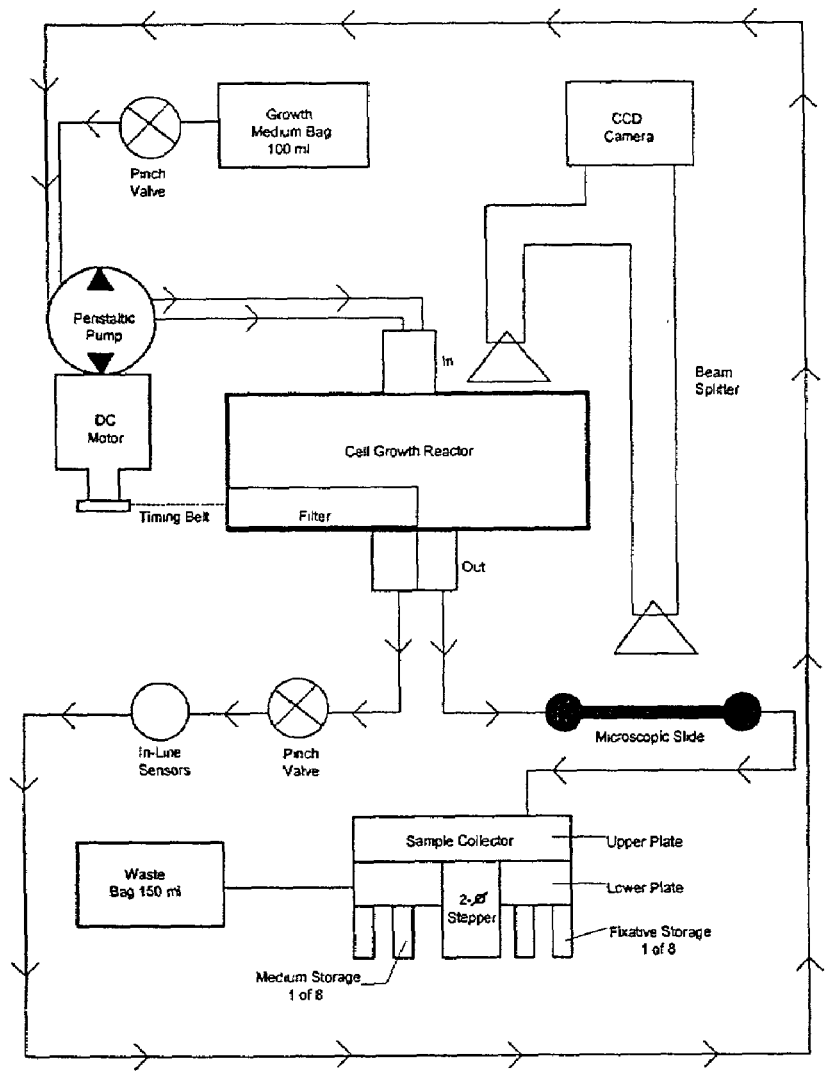
FIG. 9 is a flow diagram of the present invention showing the flow path of the fluid and cells through the bioreactor, photo system, together with the media supply bag and sample collection and waste containers.

The upper rotary union is a single-pass channel that permits fresh medium to be delivered to the cell growth reactor while the lower rotary union has two independent exit channels. The fluid flow block diagram is shown best in FIGS. 5 and 9. The channels in the lower rotary union allow either filtered or unfiltered medium to pass out of the cell growth reactor. The filtered medium does not carry any cells within the solution while the unfiltered medium contains live cells. The filtered medium is used for oxygenation of the cell growth reactor by passing solution through 60-cm of thin-walled silicone tubing which is exposed to an ambient or oxygen enriched environment. In addition, the filtered medium passes over the sensors which provide pH and dissolved oxygen (DO) measurements. However, it is contemplated that samples could be collected and analyzed for pH, glucose, and dissolved oxygen. The unfiltered medium passes through the microscopic observation slide and on to the rotary cell sample collector.

The video concept provides observation capability of the bioreactor as well as microscopic observation of individual cells. Due to the space constraints within the space-flight cassette, both miniaturization and optimization of this system comprises a significant innovation. The entire camera and microscope system must fit within a volume of approximately 4×2×10 centimeters.

Figure 10:
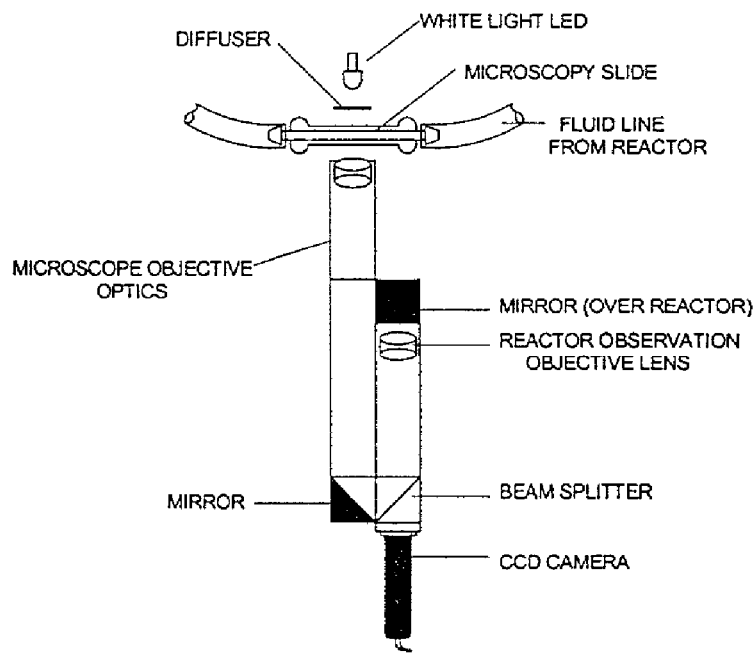
FIG. 10 is a top view of a photo device for the present invention for viewing the cells in suspension in macro or micro view.

The camera illustrated in FIG. 10 utilizes a dual optical path configuration and a single ½ inch color CCD camera or video plane for both optical systems. One optical path will allow observation of the rotating cell growth reactor contents with a 20×25 mm Field Of View (FOV). The other microscopic observation path will provide a 4×5 mm FOV with approximately 5-micron resolution of cell samples that have been extracted from the bioreactor and pumped into the observation cell (see below). The candidate resolution for the microscopic system is based on a 12-micron pixel size.

A digital camera and/or video device could be used to show instantaneous or still frame pictures. The ELMO camera system in this embodiment has a remote miniature camera head, which contains the CCD and a separate controller. The controller is located outside of the space-flight cassette. The camera head is attached to housing containing a 12.5 mm beamsplitter cube. One side of the beamsplitter is attached to an objective lens, which views one side of the bioreactor volume through a turning prism. The prism is enclosed to prevent contamination of the Total Internal Reflection (TIR) surface. The viewing surface of the prism can be heated slightly using a Minco (or equivalent) foil type heater to prevent condensation (the interior of the cassette is maintained at high relative humidity). The other side of the beamsplitter is attached to a spacer barrel, which is attached to the microscopic observation slide. The spacer tube provides the path length required between the CCD and the objective lens to achieve the desired magnification or FOV. The space between the objective lens and the observation cell surface is sealed and back-filled with dry nitrogen to prevent condensation. Other air spaces within the video system optics is sealed and backfilled with dry nitrogen.

Connection between the camera cable from the camera head in the cassette and the external camera controller is made using a separate connector in the housing of the cassette. Camera images are stored digitally using a frame grabber PC104 board in the precessing facility shown in FIG. 16. Image capture is controlled by a programmed routine. The current candidate frame grabber PC104 board is from Image Nation.

Figure 11:
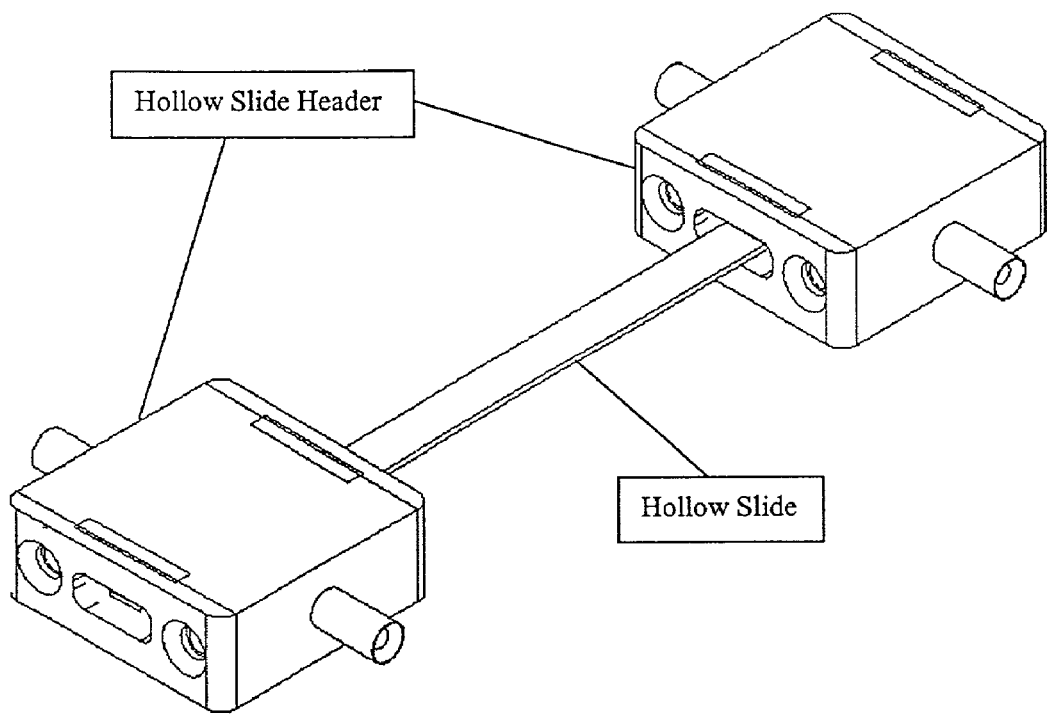
FIG. 11 is a perspective view of a microscopic observation slide developed for the photo system of the present invention showing the slide endcaps for attaching to the tubing from the rotary cell reactor and the rotary cell sample collector.
Figure 12:
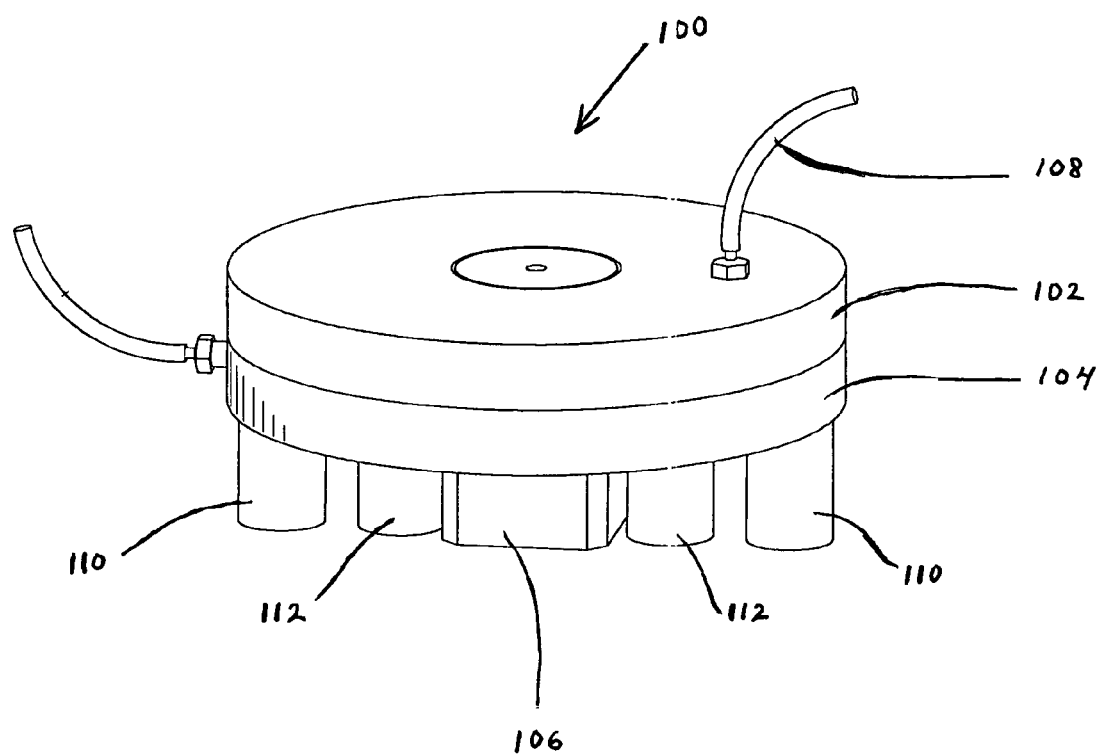
FIG. 12 is a perspective view showing the lower plate of the rotary cell sample collection held stationary while the upper plate is rotated by the stepping motor.

A modular slide system that is utilized for each observation application has been developed. Slide material selection is critical in slide development (see FIG. 11). Glass, polycarbonate, and various other materials are interchangeable depending upon the physical requirements and environments of operation of the unit. The superior optical clarity, biocompatability, chemical compatibility, low cost, and ready availability of glass made it the preferred choice for the microscopic observation slide. The only shortfall of glass is that it is a shatterable material and would pose several design issues for space flight applications.

The LEDs utilized in this hardware will be responsible for providing uniform light to the cell growth reactor as well as the microscopic observation slide. From our examination of the spectral distribution of the LEDs required for video observations of the cells, it has been determined that only white light is required; however, radiation of other wavelengths may be utilized for particular applications. LEDs are available that are able to meet the spectral distribution of 430 to 690 nm. The other advantages of LEDs are the reliability and the low thermal impact on the overall system without the EMI and containment issues associated with fluorescence. LEDs are now available with spectral distribution curves that approximate white light. Of course, means of lighting such as conventional types of light emitting devices may be utilized especially in earth applications wherein the energy and weight considerations are of less importance as compared to the cost savings.

Selection of the camera view between the cell growth reactor and the microscopic observation slide is made by turning on or off the appropriate light source. To observe the cells in the microscopic observation slide, the reactor light is turned off and the microscopic slide backlight is turned on. The microscopic observation slide is backlighted using a single LED and a diffuser. Backlighting is not possible for the bioreactor due to its design. The bioreactor, therefore, is illuminated by selection of two LEDs providing front lighting or two LED's providing oblique lighting. This approach allows the camera to see the image from the reactor.

A novel rotary cell sample collector 100 for space-flight applications (see FIGS. 7, 9, 12, and 13) provides the capability to collect and fix cell samples upon demand via telemetry or pre-programmed time lines. The rotary cell sample collector 100 utilizes two plates 102 and 104 clamped together at their centers and sealed with a grease such as vacuum grease or other low solubility and low vapor pressure grease such as a silicone grease. The lower plate 104 remains stationary while the upper plate 102 is rotated by the stepping motor 106. The upper plate 102 is rotated by a two-phase flight-proven stepping motor 106 that provides precise control for proper alignment. The cells and medium exit the reactor vessel 20 at the lower rotary union 1 on the unfiltered side after additional medium is added upstream to the cell growth reactor 20. Then, the cells and medium pass through the microscopic observation slide 90, and then on to the rotary cell sample collector 100.

Figure 13:
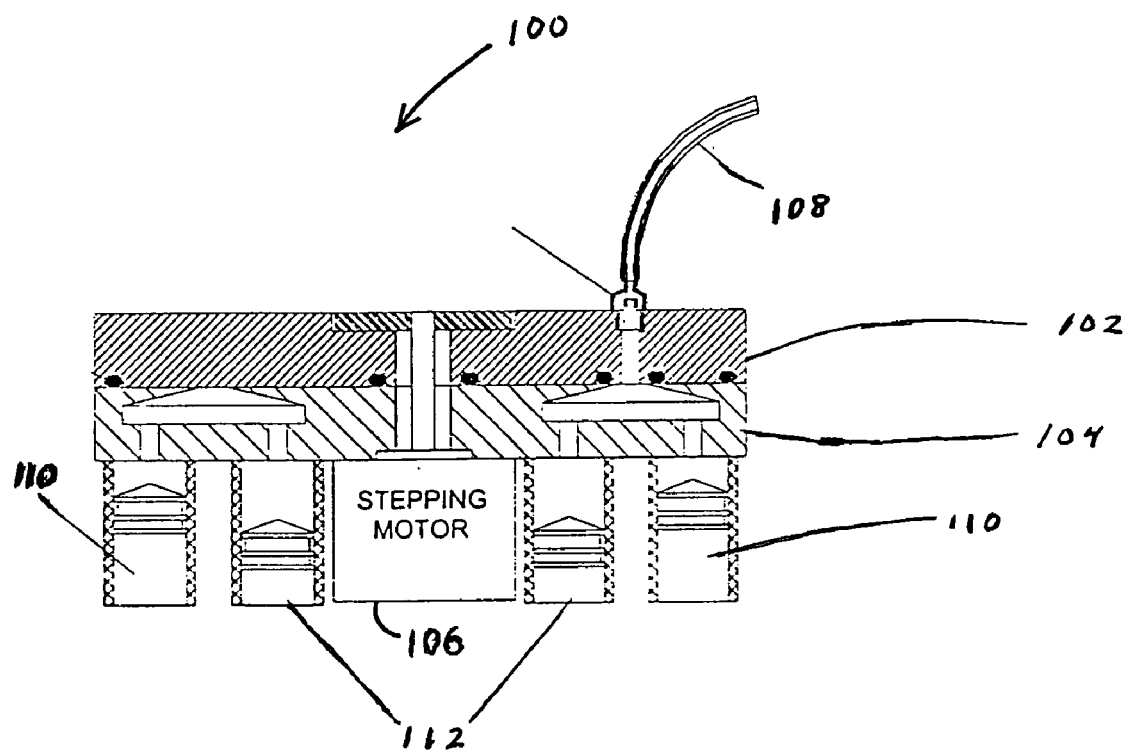
FIG. 13 is a diagram depicting the sample collection syringes mounted to the lower plate.

The cells and medium enter the rotary cell sample collector upper plate 102 at one location via a threaded hose barb (see FIG. 13). In order to avoid the use of fluid unions, the upper plate 102 is only permitted to rotate 360° to prevent the inlet line 108 from becoming unattached or twisted. The single inlet located in the upper plate 102 delivers the cells and medium directly to a pair of collection syringes 110 and 112 mounted on the lower plate 104. Collection in syringes (cylinders with movable pistons) has been chosen over collection in bags. Of course it is contemplated the cuvettes or other collection containers may be utilized as well. One sample syringe 110 is used to collect the medium while the other syringe 112 contains fixative used to preserve the cells such as formaldehyde or other chemical reagent. A pinch valve is opened, and the medium is forced into the collection syringe. Once the medium has been collected, the pinch valve for the fixative is opened, and fixative is forced over the cells. This technique lifts the cells off the filter to provide optimal cell fixation. Both syringes are easily removed to provide convenient access to the samples following an experiment.

One of the main technical challenges is to provide the capability to flush the feed lines and be guaranteed fresh medium and live cells enter the cell collection syringe. In order to flush the line before sample collection, the upper plate is aligned over a waste hole in the lower plate. The hole is plumbed directly to the waste bag located downstream from the rotary cell sample collector. Therefore, before a sample is collected, the upper plate is aligned over a through hole and the line is flushed free of any dead cells or spent medium. When it is time to collect a sample (See FIG. 7), the lines are flushed out and then the upper plate is rotated over to the next set of sample collection syringes. First, the pinch valve is opened for the medium collection. The cells and medium are pumped into the chamber. A layer of filter material prevents the cells from entering into the medium collection syringe. After the medium has been collected into the syringe, the pinch valve is closed. Next, the pinch valve for the cell fixative is opened. The pressure generated by the compressed spring pushes the plunger up and the fixative lifts the cells off the filter material. To equalize the pressure, the cells flow into the backside of the fixative syringe. After the sample is collected, the upper plate is rotated to the next opening, which allows cells and medium to be passed through the microscopic observation slide, if desired, and on to the waste bag. This flow path can be activated multiple times until it is time to collect another sample.

More particularly, as illustrated in FIG. 7 the sequence for the rotary cell sample collector is as follows:

a) Position of the collection syringes before a sample is collected;

b) The pinch valve for the sample of medium and cells is opened, the cells remain on the filter material while the medium pushes the syringe plunger down, and the pinch valve is closed;

c) The pinch valve for the fixative syringe is opened, and the fixative flow lifts the cells off the filter material, and the pressure forces the liquid to the backside of the syringe.

Figure 14:
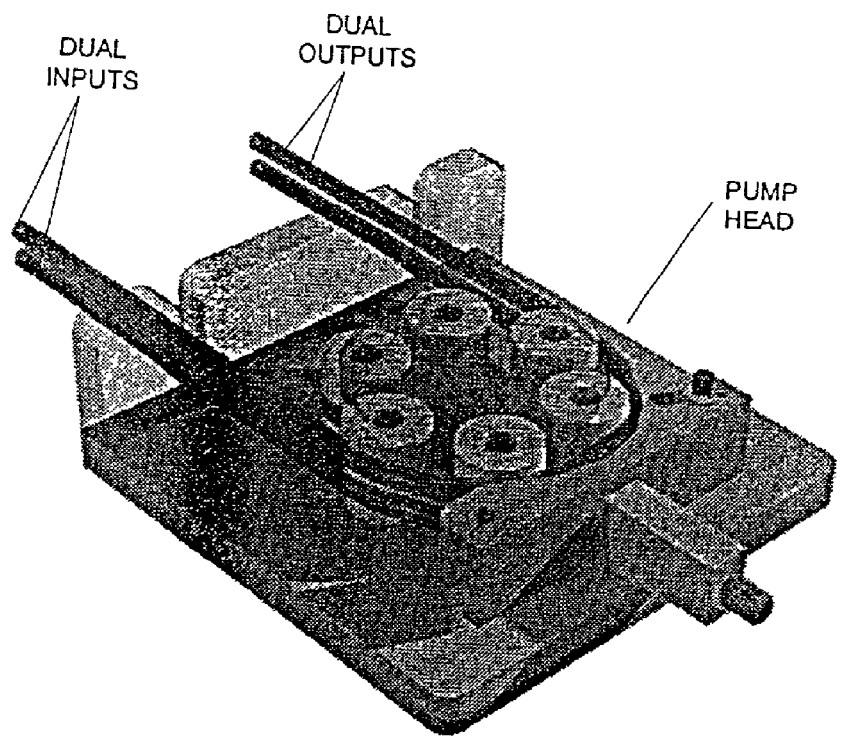
FIG. 14 is a perspective view of a miniature peristaltic pump developed for the present invention.

It is important that the system incorporate means to determine the optimal technique for delivering multiple fluids to multiple locations. A peristaltic pump as best illustrated in FIG. 14 was designed to fit the present application. In preference over stepper motors and micro pumps a conceptual design for a new miniature peristaltic pump was developed. The pump was designed so it could deliver controlled amounts of growth medium as well as circulate medium in and out of the cell growth reactor for oxygenation. The fluid system was designed with pinch valves located upstream of the miniature peristaltic pump to prevent the liquid from flowing through the pump except when the valves are open.

The miniature peristaltic pump has the capability to deliver precise amounts of medium into the cell growth reactor. The pump can deliver quantities as small as 0.015 cc. This type of precision is extremely critical for the overall operation of the system because pumping new growth medium into the cell growth reactor also pumps medium with live cells into the microscopic observation slide and the rotary cell sample collector.

The present invention can be fabricated as a stand alone instrument or incorporated into a family of cassette that includes a unit within a processing facility (see FIG. 16). This family of units consists of modules or cassettes as shown in FIG. 15, all of which are designed for accommodation in and control by BIOTEC. a fully automated, multi-use bioprocessing thermal environment controller for the processing of biological samples in space or utilized in earth laboratories. It is a single-locker facility designed for accommodation in the Shuttle Middeck, Spacehab locker, and/or Space Station EXPRESS rack. This modular system facilitates a range of biotechnology processes all of which are applicable to earth research and development.

The BIOTEC flight processing facility contains independently controlled processing modules or cassettes that can either be programmed for totally automated operation, or controlled via telemetry for real-time telescience and telerobotic operation. The processing temperature can be independently controlled and regulated between 4–40° C. in each of the processing modules. Biological samples for processing are loaded (preflight, on the ground) into specially designed containers, which are housed within a compact cassette that provides an appropriate level of containment for processing in the processing facility.

The instant bioreactor, when utilized in a cassette will be designed to operate within the space-flight instrument referred to as a BIOTEC facility consisting of a group of identical spaceborne processing modules designed to accommodate a family of cassettes having identical envelopes. Each cassette accommodates a specific type of biotechnology experiment, such as crystallization, separations or cell cultivation. Each cassette interfaces with the BIOTEC computer and power via a smart multi-pin connector, and the BIOTEC processing module responds automatically with a sequenced experiment protocol for each cassette.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplifications presented hereinabove. Rather, what is intended to be covered is within the spirit and scope of the appended claims.

We claim:

1. A bioreactor apparatus and cell culturing system providing means for cell sampling, dilution, and fixation, comprising:
   a sealed housing enclosing a cell growth reactor vessel;
   said cell growth reactor vessel rotatable about its axis including a cylindrical side wall connecting a first reactor cover plate and a second reactor cover plate, a first fluid rotary union in said first reactor cover plate providing an inlet for fluid communication with a fluid medium source, a second fluid rotary union in said second reactor cover plate including at least one exit outlet for medium and cells and at least one exit outlet in fluid communication with a filter for retaining cells and passage of medium;
   means for rotating said reactor vessel about its axis;
   means for collecting fluid and cell samples comprising a rotary sample collector including a first stationary collector plate and a second rotatable collector plate in sealed connection at their centers and in fluid communication with said exit outlet for medium and cells;
   said rotary sample collector comprising multiple sample collectors in said first stationary collector plate which are alignable with an inlet in said second rotatable collector plate with capability for collecting cells on filters, fixing the cells and collecting the cells;
   means for delivering medium and circulating medium to and from said reactor vessel;
   means for controlling the humidity within said sealed housing;
   means for rotating said second rotatable collector plate;
   a computer with graphical user interface for automatically and/or robotically controlling rotation of the reactor vessel, rotation of said second plate, controlling the feeding of fresh medium, controlling perfusing the reactor vessel, controlling taking timed collection samples of fluid from said reactor vessel, and selecting between collecting cells or cell-free supernatant; and
   an electrical power source in electrical communication with said means for rotating said reactor vessel, said means for rotating said second collector plate, and said means for delivering and circulating medium.

2. The bioreactor apparatus and cell culturing system of claim 1 said first stationary collector plate including a compartment with a filter means to remove waste liquid from an input cell suspension, means for collecting cells in chambers in liquid suspension, and means to store fixed cells for later recovery and examination.

3. The bioreactor apparatus and cell culturing system of claim 1 further including means for exchanging gases between said cells in said medium and ambient gases comprising a selected length of gas permeable tubing in fluid communication with said cells in said medium and said ambient gas.

4. The bioreactor and cell culturing system of claim 1 wherein said filter comprises a low pressure drop filter for preventing cells from exiting the reactor when fluid is withdrawn.

5. The bioreactor apparatus and cell culturing system of claim 4, wherein said low pressure drop filter is a polymeric filter.

6. The bioreactor apparatus and cell culturing system of claim 1 further including a polymeric fresh-medium storage bag in fluid communication with a peristaltic pump for batch feeding, perfusion or sample collection connecting to said inlet of said reactor vessel through a conduit.

7. The bioreactor apparatus and cell culturing system of claim 1 wherein said means for controlling the humidity comprises a humidity control system consisting of a polymeric porous matrix and a fan.

8. The bioreactor apparatus and cell culturing system of claim 1 including means for oxygenation of said medium in said reactor.

9. The bioreactor apparatus and cell culturing system of claim 1 further including analytical sensors for measuring the pH, glucose, and oxygen of said medium.

10. The bioreactor apparatus and cell culturing system of claim 1 said means for rotating said second rotatable collector plate comprises a stepping motor for rotating and aligning said second rotatable collector plate with said first stationary collector plate.

11. The bioreactor apparatus and cell culturing system of claim 1, said means for delivering medium and circulating medium to and from said reactor vessel comprises at least one perfusion pump.

12. The bioreactor apparatus and cell culturing system of claim 1, further comprising:
   a camera and an observation system, comprising:
      a video frame grabber;
      a beam splitter for dual optical view of contents of said rotating cell growth reactor and of cell samples extracted from said cell growth reactor or a microscopic observation slide disposed in a fluid line from said reactor vessel;
      at least one LED and a diffuser for providing backlighting for said microscopic observation slide;
      at least one LED providing front lighting or oblique lighting for viewing the contents of said cell growth reactor;
      a camera attached to said video frame grabber and said beam splitter wherein a first side of said beam splitter attached to an objective lens for viewing said reactor contents and a second side of said beam splitter attached to a spacer barrel which is attached to said microscopic observation slide.

13. The bioreactor apparatus and cell culturing system of claim 12, wherein said camera system comprises a color camera and a dual optical path configuration allowing for a first observation of the rotating cell growth reactor contents with a 20×25 mm Field Of View (FOV) and a second microscopic observation path providing an approximately 5-micron resolution of cell samples that have been extracted from the reactor vessel and pumped into the observation slide.

14. The bioreactor apparatus of claim 13, wherein said camera in said camera system is a digital camera andlor a video device for showing instantaneous or still frame pictures.

15. The bioreactor apparatus of claim 12 further comprising a turning prism in optical communication with said cell growth reactor vessel and a foil type heater in radiant communication with said turning prism to prevent condensation.

16. The bioreactor and cell culture system of claim 1, further including means for oxygenation of medium in said cell growth reactor vessel comprises passing filtered medium through thin-walled silicone tubing in an oxygen rich environment.

17. A closed-loop bioreactor apparatus and cell culturing system, comprising:
a cell growth reactor vessel rotatable about its axis including a cylindrical side wall connecting a first reactor cover plate and a second reactor cover plate, a first fluid rotary union in said first reactor cover plate providing an inlet for fluid communication with a fluid medium source, a second fluid rotary union in said second reactor cover plate including at least one exit outlet for medium and cells and at least one exit outlet in fluid communication with a filter for retaining cells and passage of medium;
means for rotating said reactor vessel about its axis;
means for collecting fluid and cell samples comprising a rotary sample collector including a first stationary collector plate and a second rotatable collector plate in sealed connection at their centers and in fluid communication with said exit outlet for medium and cells;
said rotary sample collector further comprises means for rotating an inlet in second rotatable collector plate into a compartment in said first stationary collector plate with filter means to remove waste liquid from an input cell suspension, means for collecting cells in chambers in liquid suspension, and means to store fixed cells for later recovery and examination;
means for delivering medium and circulating medium to and from said reactor vessel to form a closed loop;
means for rotating said second rotatable collector plate;
means for exchanging gases between said medium and ambient gas environments;
a computer with graphical user interface for automatically and/or robotically controlling said reactor vessel;
an observation system wherein said observation system comprises a camera and a dual optical path configuration allowing for an observation of said cell growth reactor vessel contents and a second microscopic observation path with a 5-micron resolution of said cell sample;
an electrical power source in electrical communication with said means for rotating said reactor vessel, said means for rotating said second collector plate, and said means for delivering and circulating medium.

18. The bioreactor and cell-culture system according to claim 17, wherein said reactor vessel comprises at least two external tubing connectors that articulate said reactor vessel with said closed loop.

19. The bioreactor and cell-culture system according to claim 18 wherein fluid movement within said closed loop is effected by at least one peristaltic, shuttle or similar pumps that act upon the tubing of the closed loop and do not contact the fluid directly.

20. The bioreactor and cell-culture system according to claim 19 wherein said fluid movement is controlled by at least one electronically controlled pinch valves that acts upon the tubing of the closed loop and does not contact the fluid directly.

21. The bioreactor and cell-culture system according to claim 18 wherein said closed-loop bioreactor system is fully enclosed in a first sealed compartment providing a level of chemical containment for safely and in which containers used for sample collection are optionally enclosed within a second sealed container within said first sealed container for one additional level of chemical containment and therefore triple chemical containment for safety.

22. The bioreactor and cell-culturing system according to claim 18 wherein said closed fluid loop includes a plurality of lines providing access for the addition of external fluid to said closed loop and the removal of waste and samples from said closed loop without violating two levels of chemical containment for safety, for making chemical measurements on line, for collecting and fixing cells automatically, for immediate observation by an optionally included microscope, and for collection in sample containers.

23. The bioreactor and cell-culture system according to claim 17 further comprising means for measuring pH and dissolved oxygen content of said medium from said reactor vessel.

24. The bioreactor and cell-culture system according to claim 17 wherein said computer includes programming for conducting sequences of experimental procedure requiring pumping, valving, chemical measurement, reactor rotating rate, microscope operation without operator intervention or with optional operator intervention.

25. The bioreactor and cell-culture system according to claim 17 wherein said bioreactor and cell-culture system is capable of functioning in low gravity and that fulfills safety requirements for manned space flight.

26. The bioreactor and cell-culture system according to claim 17 wherein said second microscopic observation path further comprises:
a microscope system for observing suspended cells or organisms within said reactor vessel, said microscope system comprising an inlet from a branch of the closed loop coupled to a holder for a hollow microscope slide, a hollow microscope slide made of glass or fabricated by photo polymerization, a light-microscope objective compound lens, a video plane, an outlet for the removal of samples of fluid after observation, and reservoirs for the addition of reagents to cell suspensions when said reagents are required for observation.

* * * * *

UNITED STATES PATENT AND TRADEMARK OFFICE
CERTIFICATE OF CORRECTION

PATENT NO. : 7,198,940 B2 Page 1 of 1
APPLICATION NO. : 10/003481
DATED : April 3, 2007
INVENTOR(S) : John C. Vellinger et al.

It is certified that error appears in the above-identified patent and that said Letters Patent is hereby corrected as shown below:

On the title page, the line which reads:

(73) Assignee: Shot Hardware Optimization Technology, INC., Greenville, IN (US)

should be changed to:

(73) Assignee: Space Hardware Optimization Technology, INC., Greenville, IN (US)

Signed and Sealed this

Seventeenth Day of June, 2008

JON W. DUDAS
*Director of the United States Patent and Trademark Office*